(12) United States Patent
Senaratne et al.

(10) Patent No.: US 9,885,063 B2
(45) Date of Patent: Feb. 6, 2018

(54) PROCESS FOR FERMENTING CO-CONTAINING GASEOUS SUBSTRATES IN A LOW PHOSPHATE MEDIUM EFFECTIVE FOR REDUCING WATER USAGE

(71) Applicant: INEOS BIO SA, Rolle (CH)

(72) Inventors: Ryan H. Senaratne, Fayetteville, AR (US); Peter Simpson Bell, Dunblane (GB); Song Liu, Fayetteville, AR (US); Syrona R. Scott, Fayetteville, AR (US)

( * ) Notice: Subject to any disclaimer, the term of this patent is extended or adjusted under 35 U.S.C. 154(b) by 0 days.

(21) Appl. No.: 14/293,111

(22) Filed: Jun. 2, 2014

(65) Prior Publication Data

US 2014/0363867 A1 Dec. 11, 2014

Related U.S. Application Data

(60) Provisional application No. 61/833,240, filed on Jun. 10, 2013.

(51) Int. Cl.
| | |
|---|---|
| *C12P 7/06* | (2006.01) |
| *C12P 7/08* | (2006.01) |
| *C12P 7/16* | (2006.01) |
| *C12N 1/20* | (2006.01) |
| *C12N 1/00* | (2006.01) |

(52) U.S. Cl.
CPC ............. *C12P 7/065* (2013.01); *C12N 1/00* (2013.01); *C12N 1/20* (2013.01); *C12P 7/08* (2013.01); *C12P 7/16* (2013.01); *Y02E 50/10* (2013.01); *Y02E 50/17* (2013.01)

(58) Field of Classification Search
None
See application file for complete search history.

(56) References Cited

U.S. PATENT DOCUMENTS

2010/0227377 A1* 9/2010 Adams .............. C12N 1/20
435/252.7

FOREIGN PATENT DOCUMENTS

| JP | 11-341947 | * 12/1999 | ............... A23C 9/12 |
|---|---|---|---|
| WO | 2010064933 | 6/2010 | |
| WO | 2011028137 | 3/2011 | |
| WO | 2011112103 | 9/2011 | |
| WO | 2013147621 | 10/2013 | |

OTHER PUBLICATIONS

International Searching Authority, International Search Report and Written Opinion issued in PCT/US2014/041115, dated Dec. 4, 2014, 22 pages.
Kopke, M. et al.: "Fermentative production of ethanol from carbon monoxide", Current Opinion in Biotechnology, vol. 22, No. 3, Jun. 2011, pp. 320-325, XP055104855.

* cited by examiner

*Primary Examiner* — Karen Cochrane Carlson
*Assistant Examiner* — Jennifer M. H. Tichy
(74) *Attorney, Agent, or Firm* — James P. Krueger

(57) ABSTRACT

A process is provided for fermenting CO-containing gaseous substrates in a low phosphate medium. The process includes blending a liquid medium that includes at least one transition metal element with a liquid medium that includes at least at least one other transition metal element and one non-metal element to provide a fermentation medium. The process is effective for preventing precipitation of one or more transition metal elements with one or more non-metal elements. The fermentation medium used in the process is prepared in a way that requires significantly lower amounts of water and reduced levels of phosphate.

13 Claims, 1 Drawing Sheet

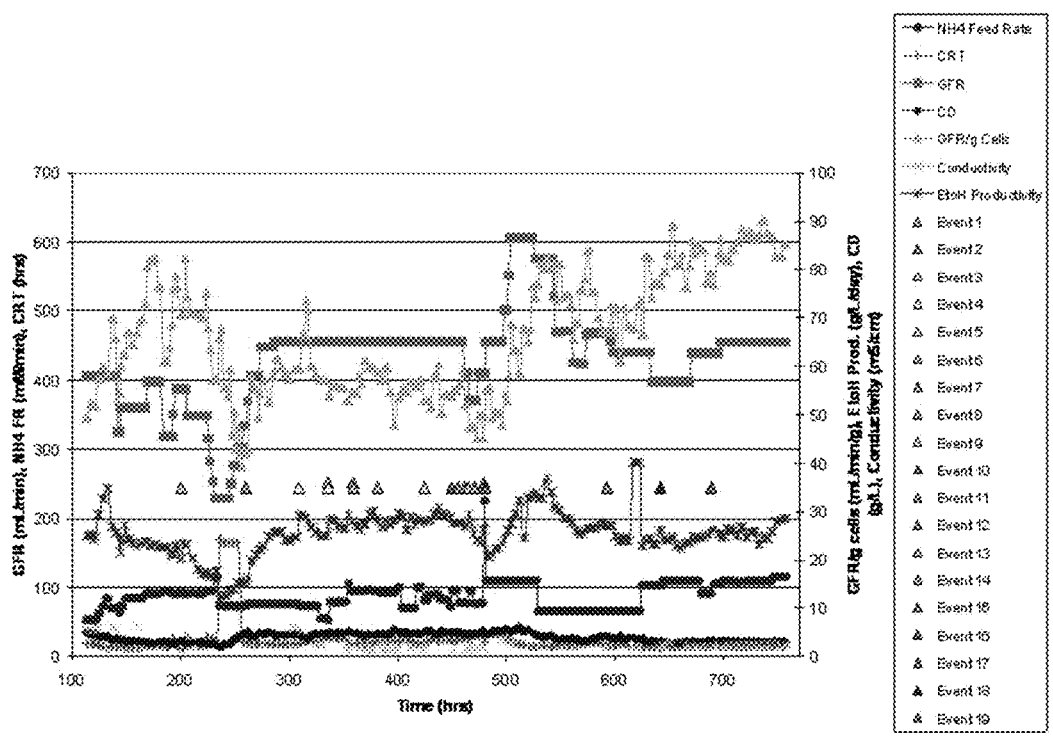

PROCESS FOR FERMENTING CO-CONTAINING GASEOUS SUBSTRATES IN A LOW PHOSPHATE MEDIUM EFFECTIVE FOR REDUCING WATER USAGE

This application claims the benefit of U.S. Provisional Application No. 61/833,240 which was filed on Jun. 10, 2013, and which is incorporated in its entirety herein by reference.

A process is provided for fermenting CO-containing gaseous substrates in a low phosphate medium. More specifically, the process includes fermenting the CO-containing gaseous substrate in a medium prepared in a way that requires lower amounts of water.

BACKGROUND

Acetogenic microorganisms can produce ethanol from carbon monoxide (CO) through fermentation of gaseous substrates. Fermentations using anaerobic microorganisms from the genus *Clostridium* produce ethanol and other useful products. For example, U.S. Pat. No. 5,173,429 describes *Clostridium ljungdahlii* ATCC No. 49587, an anaerobic microorganism that produces ethanol and acetate from synthesis gas. U.S. Pat. No. 5,807,722 describes a process and apparatus for converting waste gases into organic acids and alcohols using *Clostridium ljungdahlii* ATCC No. 55380. U.S. Pat. No. 6,136,577 describes a process and apparatus for converting waste gases into ethanol using *Clostridium ljungdahlii* ATCC No. 55988 and 55989.

Fermentation processes often require large amounts of water and nutrients. Reducing water usage, eliminating certain components, and reducing required concentrations levels of other components while maintaining alcohol productivity may provide significant cost savings, especially at a commercial scale fermentation.

SUMMARY

A process is provided for fermenting CO-containing gaseous substrates using lower amounts of water. A fermentation medium used in the process is prepared in a way that requires significantly lower amounts of water and reduced levels of phosphate.

A fermentation process includes blending a liquid medium that includes at least one transition metal element with a liquid medium that includes at least at least one other transition metal element and one non-metal element to provide a fermentation medium. The process includes contacting a CO-containing substrate with the fermentation medium and fermenting the CO-containing substrate to provide an acidic pH. The process effective for preventing precipitation of one or more transition metal elements with one of more non-metal elements and is effective for utilizing about 2 U.S. gallons of water or less provided to the fermentation medium per U.S. gallon of ethanol produced.

A process for fermenting a CO-containing substrate includes providing the CO-containing substrate to a fermentor and contacting the CO-containing substrate with a fermentation medium. The process includes providing a fermentation medium by a process that includes blending a first solution that includes one or more elements selected from the group consisting of Zn, Co and Ni with a second solution that includes one or more elements from the group consisting of W and Se in amounts effective for providing a fermentation medium having a conductivity of about 30 mS/cm or less and about 3 mM or less phosphate. Fermenting the CO-containing substrate is effective for providing an STY of 10 g total alcohol/(L·day) or more and is effective for utilizing about 2 U.S. gallons of water or less provided to the fermentation medium per U.S. gallon of ethanol produced.

In another aspect, a process for reducing water usage in preparation of a fermentation medium includes blending a solution that includes an element selected from the group consisting of one or more of Zn, Co, Ni and with a solution that includes an element from the group consisting of one or more of W, Se in amounts effective for providing a fermentation medium having a conductivity of about 30 mS/cm or less. The fermentation medium requires about 10% to about 40% less water than a fermentation medium having more than about 3 mM phosphate.

BRIEF DESCRIPTION OF FIGURES

The above and other aspects, features and advantages of several aspects of the process will be more apparent from the following FIGURE.

FIG. 1 illustrates performance of a steady state *Clostridium ljungdahlii* culture on a low phosphate medium and the use of $NH_4OH$ as base to control pH and act as a nitrogen source.

DETAILED DESCRIPTION

The following description is not to be taken in a limiting sense, but is made merely for the purpose of describing the general principles of exemplary embodiments. The scope of the invention should be determined with reference to the claims.

In one aspect, nutrient levels in a nutrient feed to the fermentor are optimized such that the % consumption of each nutrient by the acetogenic bacteria in the fermentor are essentially equal. Unexpectedly, imbalances in the amounts of nutrients consumed and resulting residual amounts of nutrients in the medium result in increased conductivity and decline in fermentation performance. In order to alleviate increased conductivity, large amounts of water were required. Careful balancing of nutrients provided and nutrients consumed result in reduced water usage and reduced nutrient usage. In this aspect, the nutrient medium and fermentation process optimizes nutrient utilization such that 90% or more of the nutrients are utilized, and in another aspect, at least about 95% or more of the nutrients are utilized.

Syngas fermentations conducted in bioreactors with medium and acetogenic bacteria as described herein are effective for providing conversions of CO in syngas into alcohols and other products. In this aspect, productivity may be expressed as STY (space time yield expressed as g total alcohol/(L·day). In this aspect, the process is effective for providing a STY (space time yield) of at least about 10 g or more total alcohol/(L·day). Possible STY values include about 10 g total alcohol/(L·day) to about 200 g total alcohol/(L·day), in another aspect, about 10 g total alcohol/(L·day) to about 160 g total alcohol/(L·day), in another aspect, about 10 g total alcohol/(L·day) to about 120 g total alcohol/(L·day), in another aspect, about 10 g total alcohol/(L·day) to about 80 g total alcohol/(L·day), in another aspect, about 20 g total alcohol/(L·day) to about 140 g total alcohol/(L·day), in another aspect, about 20 g total alcohol/(L·day) to about 100 g total alcohol/(L·day), in another aspect, about 40 g total alcohol/(L·day) to about 140 g total alcohol/

(L·day), and in another aspect, about 40 g total alcohol/(L·day) to about 100 g total alcohol/(L·day).

Definitions

Unless otherwise defined, the following terms as used throughout this specification for the present disclosure are defined as follows and can include either the singular or plural forms of definitions below defined:

The term "about" modifying any amount refers to the variation in that amount encountered in real world conditions, e.g., in the lab, pilot plant, or production facility. For example, an amount of an ingredient or measurement employed in a mixture or quantity when modified by "about" includes the variation and degree of care typically employed in measuring in an experimental condition in production plant or lab. For example, the amount of a component of a product when modified by "about" includes the variation between batches in a multiple experiments in the plant or lab and the variation inherent in the analytical method. Whether or not modified by "about," the amounts include equivalents to those amounts. Any quantity stated herein and modified by "about" can also be employed in the present disclosure as the amount not modified by "about".

The term "gaseous substrate" is used in a non-limiting sense to include substrates containing or derived from one or more gases.

The term "syngas" or "synthesis gas" means synthesis gas which is the name given to a gas mixture that contains varying amounts of carbon monoxide and hydrogen. Examples of production methods include steam reforming of natural gas or hydrocarbons to produce hydrogen, the gasification of coal and in some types of waste-to-energy gasification facilities. The name comes from their use as intermediates in creating synthetic natural gas (SNG) and for producing ammonia or methanol. Syngas is combustible and is often used as a fuel source or as an intermediate for the production of other chemicals.

The term "fermentor" includes a fermentation device consisting of one or more vessels and/or towers or piping arrangements, which includes the Continuous Stirred Tank Reactor (CSTR), Immobilized Cell Reactor (ICR), Trickle Bed Reactor (TBR), Moving Bed Biofilm Reactor (MBBR), Bubble Column, Gas Lift Fermenter, Membrane Reactor such as Hollow Fibre Membrane Bioreactor (HFMBR), Static Mixer, or other vessel or other device suitable for gas-liquid contact.

The terms "fermentation", fermentation process" or "fermentation reaction" and the like are intended to encompass both the growth phase and product biosynthesis phase of the process. In one aspect, fermentation refers to conversion of CO to alcohol.

The term "cell density" means mass of microorganism cells per unit volume of fermentation broth, for example, grams/liter.

The term "increasing the efficiency", "increased efficiency" and the like, when used in relation to a fermentation process includes increasing one or more of the rate of growth of microorganisms in the fermentation, the volume or mass of desired product (such as alcohols) produced per volume or mass of substrate (such as carbon monoxide) consumed, the rate of production or level of production of the desired product, and the relative proportion of the desired product produced compared with other by-products of fermentation.

As used herein, "total alcohol" includes ethanol, butanol, propanol and methanol. In one aspect, the total alcohol may include at least about 75 weight percent or more ethanol, in another aspect, about 80 weight percent or more ethanol, in another aspect, about 85 weight percent or more ethanol, in another aspect, about 90 weight percent or more ethanol, and in another aspect, about 95 weight percent or more ethanol. In another aspect, total alcohol may include about 25 weight percent or less butanol.

The term "specific CO uptake" means an amount of CO in mmoles consumed by unit mass of microorganism cells (g) per unit time in minutes, i.e. mmole/gram/minute.

CO-Containing Substrate

A CO-containing substrate may include any gas that includes CO. In this aspect, a CO-containing gas may include syngas, industrial gases, and mixtures thereof.

Syngas may be provided from any know source. In one aspect, syngas may be sourced from gasification of carbonaceous materials. Gasification involves partial combustion of biomass in a restricted supply of oxygen. The resultant gas mainly includes CO and $H_2$. In this aspect, syngas will contain at least about 10 mole % CO, in one aspect, at least about 20 mole %, in one aspect, about 10 to about 100 mole %, in another aspect, about 20 to about 100 mole % CO, in another aspect, about 30 to about 90 mole % CO, in another aspect, about 40 to about 80 mole % CO, and in another aspect, about 50 to about 70 mole % CO. Some examples of suitable gasification methods and apparatus are provided in U.S. Ser. Nos. 61/516,667, 61/516,704 and 61/516,646, all of which were filed on Apr. 6, 2011, and in U.S. Ser. Nos. 13/427,144, 13/427,193 and Ser. No. 13/427,247, all of which were filed on Mar. 22, 2012, and all of which are incorporated herein by reference.

In another aspect, the process has applicability to supporting the production of alcohol from gaseous substrates such as high volume CO-containing industrial flue gases. In some aspects, a gas that includes CO is derived from carbon containing waste, for example, industrial waste gases or from the gasification of other wastes. As such, the processes represent effective processes for capturing carbon that would otherwise be exhausted into the environment. Examples of industrial flue gases include gases produced during ferrous metal products manufacturing, non-ferrous products manufacturing, petroleum refining processes, gasification of coal, gasification of biomass, electric power production, carbon black production, ammonia production, methanol production and coke manufacturing.

Depending on the composition of the CO-containing substrate, the CO-containing substrate may be provided directly to a fermentation process or may be further modified to include an appropriate $H_2$ to CO molar ratio. In one aspect, CO-containing substrate provided to the fermentor has an $H_2$ to CO molar ratio of about 0.2 or more, in another aspect, about 0.25 or more, and in another aspect, about 0.5 or more. In another aspect, CO-containing substrate provided to the fermentor may include about 40 mole percent or more CO plus $H_2$ and about 30 mole percent or less CO, in another aspect, about 50 mole percent or more CO plus $H_2$ and about 35 mole percent or less CO, and in another aspect, about 80 mole percent or more CO plus $H_2$ and about 20 mole percent or less CO.

In one aspect, the CO-containing substrate mainly includes CO and $H_2$. In this aspect, the CO-containing substrate will contain at least about 10 mole % CO, in one aspect, at least about 20 mole %, in one aspect, about 10 to about 100 mole %, in another aspect, about 20 to about 100 mole % CO, in another aspect, about 30 to about 90 mole % CO, in another aspect, about 40 to about 80 mole % CO, and in another aspect, about 50 to about 70 mole % CO. The CO-containing substrate will have a $CO/CO_2$ ratio of at least about 0.75, in another aspect, at least about 1.0, and in another aspect, at least about 1.5.

In one aspect, a gas separator is configured to substantially separate at least one portion of the gas stream, wherein the portion includes one or more components. For example, the gas separator may separate $CO_2$ from a gas stream comprising the following components: CO, $CO_2$, $H_2$, wherein the $CO_2$ may be passed to a $CO_2$ remover and the remainder of the gas stream (comprising CO and $H_2$) may be passed to a bioreactor. Any gas separator known in the art may be utilized. In this aspect, syngas provided to the fermentor will have about 10 mole % or less $CO_2$, in another aspect, about 1 mole % or less $CO_2$, and in another aspect, about 0.1 mole % or less $CO_2$.

Certain gas streams may include a high concentration of CO and low concentrations of $H_2$. In one aspect, it may be desirable to optimize the composition of the substrate stream in order to achieve higher efficiency of alcohol production and/or overall carbon capture. For example, the concentration of $H_2$ in the substrate stream may be increased before the stream is passed to the bioreactor.

According to particular aspects of the invention, streams from two or more sources can be combined and/or blended to produce a desirable and/or optimized substrate stream. For example, a stream comprising a high concentration of CO, such as the exhaust from a steel mill converter, can be combined with a stream comprising high concentrations of $H_2$, such as the off-gas from a steel mill coke oven.

Depending on the composition of the gaseous CO-containing substrate, it may also be desirable to treat it to remove any undesired impurities, such as dust particles before introducing it to the fermentation. For example, the gaseous substrate may be filtered or scrubbed using known methods.

Bioreactor Design and Operation

Descriptions of fermentor designs are described in U.S. Ser. No. 13/471,827 and Ser. No. 13/471,858, both filed May 15, 2012, and U.S. Ser. No. 13/473,167, filed May 16, 2012, all of which are incorporated herein by reference.

In accordance with one aspect, the fermentation process is started by addition of medium to the reactor vessel. Some examples of medium compositions are described in U.S. Ser. Nos. 61/650,098 and 61/650,093, filed May 22, 2012, and in U.S. Pat. No. 7,285,402, filed Jul. 23, 2001, all of which are incorporated herein by reference. The medium may be sterilized to remove undesirable microorganisms and the reactor is inoculated with the desired microorganisms. Sterilization may not always be required.

In one aspect, the microorganisms utilized include acetogenic bacteria. Examples of useful acetogenic bacteria include those of the genus *Clostridium*, such as strains of *Clostridium ljungdahlii*, including those described in WO 2000/68407, EP 117309, U.S. Pat. Nos. 5,173,429, 5,593, 886 and U.S. Pat. No. 6,368,819, WO 1998/00558 and WO 2002/08438, strains of *Clostridium autoethanogenum* (DSM 10061 and DSM 19630 of DSMZ, Germany) including those described in WO 2007/117157 and WO 2009/151342 and *Clostridium ragsdalei* (P11, ATCC BAA-622) and *Alkalibaculum bacchi* (CP11, ATCC BAA-1772) including those described respectively in U.S. Pat. No. 7,704,723 and "Biofuels and Bioproducts from Biomass-Generated Synthesis Gas", Hasan Atiyeh, presented in Oklahoma EPSCoR Annual State Conference, Apr. 29, 2010 and *Clostridium carboxidivorans* (ATCC PTA-7827) described in U.S. Patent Application No. 2007/0276447. Other suitable microorganisms includes those of the genus *Moorella*, including *Moorella* sp. HUC22-1, and those of the genus *Carboxydothermus*. Each of these references is incorporated herein by reference. Mixed cultures of two or more microorganisms may be used.

Some examples of useful bacteria include *Acetogenium kivui, Acetoanaerobium noterae, Acetobacterium woodii, Alkalibaculum bacchi* CP11 (ATCC BAA-1772), *Blautia producta, Butyribacterium methylotrophicum, Caldanaerobacter subterraneous, Caldanaerobacter subterraneous pacificus, Carboxydothermus hydrogenoformans, Clostridium aceticum, Clostridium acetobutylicum, Clostridium acetobutylicum P262* (DSM 19630 of DSMZ Germany), *Clostridium autoethanogenum* (DSM 19630 of DSMZ Germany), *Clostridium autoethanogenum* (DSM 10061 of DSMZ Germany), *Clostridium autoethanogenum* (DSM 23693 of DSMZ Germany), *Clostridium autoethanogenum* (DSM 24138 of DSMZ Germany), *Clostridium carboxidivorans* P7 (ATCC PTA-7827), *Clostridium coskatii* (ATCC PTA-10522), *Clostridium drakei, Clostridium ljungdahlii* PETC (ATCC 49587), *Clostridium ljungdahlii* ERI2 (ATCC 55380), *Clostridium ljungdahlii* C-01 (ATCC 55988), *Clostridium ljungdahlii* O-52 (ATCC 55889), *Clostridium magnum, Clostridium pasteurianum* (DSM 525 of DSMZ Germany), *Clostridium ragsdali* P11 (ATCC BAA-622), *Clostridium scatologenes, Clostridium thermoaceticum, Clostridium ultunense, Desulfotomaculum kuznetsovii, Eubacterium limosum, Geobacter sulfurreducens, Methanosarcina acetivorans, Methanosarcina barkeri, Morrella thermoacetica, Morrella thermoautotrophica, Oxobacter pfennigii, Peptostreptococcus productus, Ruminococcus productus, Thermoanaerobacter kivui*, and mixtures thereof.

The fermentation should desirably be carried out under appropriate conditions for the desired fermentation to occur (e.g. CO-to-ethanol). Reaction conditions that should be considered include pressure, temperature, gas flow rate, liquid flow rate, media pH, media redox potential, agitation rate (if using a continuous stirred tank reactor), inoculum level, maximum gas substrate concentrations to ensure that CO in the liquid phase does not become limiting, and maximum product concentrations to avoid product inhibition.

The methods of the invention can be used to sustain the viability of a microbial culture, wherein the microbial culture is limited in CO, such that the rate of transfer of CO into solution is less than the uptake rate of the culture. Such situations may arise when a substrate comprising CO is not continuously provided to the microbial culture; the mass transfer rate is low; or there is insufficient CO in a substrate stream to sustain culture vitality at optimum temperature. In such embodiments, the microbial culture will rapidly deplete the CO dissolved in the liquid nutrient medium and become substrate limited as further substrate cannot be provided fast enough.

Startup:

Upon inoculation, an initial feed gas supply rate is established effective for supplying the initial population of microorganisms. Effluent gas is analyzed to determine the content of the effluent gas. Results of gas analysis are used to control feed gas rates. In this aspect, the process provides a calculated CO concentration to initial cell density ratio of about 0.5 to about 0.9, in another aspect, about 0.6 to about 0.8, in another aspect, about 0.5 to about 0.7, and in another aspect, about 0.5 to about 0.6.

In another aspect, a fermentation process includes providing syngas to a fermentation medium in an amount effective for providing an initial calculated CO concentration in the fermentation medium of about 0.15 mM to about 0.70 mM, in another aspect, about 0.15 mM to about 0.50 mM, in another aspect, about 0.15 mM to about 0.35 mM, in another aspect, about 0.20 mM to about 0.30 mM, and in another aspect, about 0.23 mM to about 0.27 mM. The process is effective for increasing cell density as compared to a starting cell density.

Post-Startup:

Upon reaching desired levels, liquid phase and cellular material is withdrawn from the reactor and replenished with medium. The process is effective for increasing cell density to about 2.0 grams/liter or more, in another aspect, about 2 to about 30 grams/liter, in another aspect, about 2 to about 25 grams/liter, in another aspect, about 2 to about 20 grams/liter, in another aspect, about 2 to about 10 grams/liter, in another aspect, about 2 to about 8 grams/liter, in another aspect, about 3 to about 30 grams/liter, in another aspect, about 3 to about 6 grams/liter, and in another aspect, about 4 to about 5 grams/liter.

In one aspect, the process includes a fermentation medium provided by a process that includes blending a first solution that includes an element selected from the group consisting of one or more of Zn (also referred to as a poor medium), Co, Ni with a second solution that includes an element from the group consisting of one or more of W and Se in amounts effective for providing a fermentation medium having a conductivity of about 30 mS/cm or less. In another aspect, the fermentation medium has a conductivity of about 1 to about 30 mS/cm, in another aspect, about 1 to about 25 mS/cm, in another aspect, about 1 to about 20 mS/cm, in another aspect, about 1 to about 15 mS/cm, in another aspect, about 1 to about 10 mS/cm, in another aspect, about 1 to about 5 mS/cm, in another aspect, about 1 to about 4 mS/cm, in another aspect, about 1 to about 3 mS/cm, in another aspect, about 1 to about 2 mS/cm, in another aspect, about 2 to about 30 mS/cm, in another aspect, about 2 to about 25 mS/cm, in another aspect, about 2 to about 20 mS/cm, in another aspect, about 2 to about 15 mS/cm, in another aspect, about 2 to about 10 mS/cm, in another aspect, about 2 to about 5 mS/cm, about 2 to about 4 mS/cm, in another aspect, about 2 to about 3 mS/cm, in another aspect, about 3 to about 30 mS/cm, in another aspect, about 3 to about 25 mS/cm, in another aspect, about 3 to about 20 mS/cm, in another aspect, about 3 to about 15 mS/cm, in another aspect, about 3 to about 10 mS/cm, in another aspect, about 3 to about 5 mS/cm, in another aspect, about 4 to about 30 mS/cm, in another aspect, about 4 to about 25 mS/cm, in another aspect, about 4 to about 20 mS/cm, in another aspect, about 4 to about 15 mS/cm, in another aspect, about 4 to about 10 mS/cm, and in another aspect, about 4 to about 5 mS/cm.

In another aspect, the blend of elements has an optical density of about 0.70 or less at 580 nm. In another aspect, the blend has an optical density of about 0 to about 0.70, in another aspect, about 0.001 to about 0.65, in another aspect, about 0.01 to about 0.65, in another aspect, about 0.01 to about 0.50, and in another aspect, about 0.01 to about 0.45. In this aspect, turbidity may be determined by any known methods. Some examples of optical density measurements are described in the EPA Guidance Manual, Turbidity Processes, April 1999, which is incorporated herein in its entirety by reference.

In another aspect, the fermentation medium has less than about 14 mM phosphate. In a related aspect, the fermentation medium has about 2 to about 14 mM phosphate, in another aspect, about 3 to about 12 mM phosphate, in another aspect, about 3 to about 6 mM phosphate, in another aspect, about 1 to about 3 mM phosphate, in another aspect, about 1 to about 2 mM phosphate, and in another aspect, about 2 to about 3 mM phosphate.

In one aspect, the process is effective for utilizing about 2 U.S. gallons of water or less provided to the fermentation medium per U.S. gallon of ethanol. In another aspect, the process is effective for utilizing about 0.5 to about 2 gallons of water per gallon of ethanol, in another aspect, about 0.5 to about 1.8 gallons of water per gallon of ethanol, in another aspect, about 0.5 to about 1.5 gallons of water per gallon of ethanol, in another aspect, about 0.5 to about 1.35 gallons of water per gallon of ethanol, in another aspect, about 0.5 to about 1.2 gallons of water per gallon of ethanol, in another aspect, about 0.5 to about 1 gallon of water per gallon of ethanol, in another aspect, about 0.5 to about 0.9 gallons of water per gallon of ethanol, in another aspect, about 0.75 to about 2 gallons of water per gallon of ethanol, in another aspect, about 0.75 to about 1.75 gallons of water per gallon of ethanol, in another aspect, about 0.75 to about 1.5 gallons of water per gallon of ethanol, in another aspect, about 0.75 to about 1.35 gallons of water per gallon of ethanol, in another aspect, about 0.75 to about 1.2 gallons of water per gallon of ethanol, in another aspect, about 0.75 to about 1 gallon of water per gallon of ethanol, in another aspect, about 1 to about 2 gallons of water per gallon of ethanol, in another aspect, about 1 to about 1.75 gallons of water per gallon of ethanol, in another aspect, about 1 to about 1.5 gallons of water per gallon of ethanol, in another aspect, about 1 to about 1.35 gallons of water per gallon of ethanol, in another aspect, about 1 to about 1.2 gallons of water per gallon of ethanol, in another aspect, about 1.5 to about 2 gallons of water per gallon of ethanol, in another aspect, about 1.5 to about 1.75 gallons of water per gallon of ethanol, and in another aspect, about 1.75 to about 2 gallons of water per gallon of ethanol.

In another aspect, the fermentation medium requires about 10% to about 40% less water than a fermentation medium having about 3 mM or more phosphate. In another aspect, the fermentation medium requires from about 10% to about 30% less water, in another aspect, about 10% to about 20% less water, in another aspect, about 15% to about 40% less water, in another aspect, about 15% to about 30% less water, in another aspect, about 15% to about 20% less water, in another aspect, about 20% to about 40% less water, in another aspect, about 20% to about 30% less water, and in another aspect, about 25% to about 30% less water, than a fermentation medium having about 3 mM or more phosphate. In another aspect, phosphate concentrations may be about 2 to about 2.5 mM, and in another aspect about 2.5 mM to about 3.0 mM, and be effective for obtaining water reductions in the indicated ranges.

In another aspect, the fermentation medium is provided with about 0.005 µg or more per minute of Zn per gram of cells, about 0.0002 µg or more per minute of Co per gram of cells, about 0.003 µg or more per minute of Ni per gram of cells, about 0.039 µg or more per minute of W per gram of cells, and about 0.001 µg or more per minute of Se per gram of cells. In this aspect, the fermentation medium may include the following amounts of one or more of the following:

Zn: in one aspect, about 0.005 to about 0.11 µg per minute per gram of cells, in another aspect, about 0.005 to about 0.09 µg per minute per gram of cells, in another aspect, about 0.005 to about 0.065 µg per minute per gram of cells, in another aspect, about 0.005 to about 0.04 µg per minute per gram of cells, in another aspect, about 0.01 to about 0.075 µg per minute per gram of cells, in another aspect, about 0.01 to about 0.055 µg per minute per gram of cells, in another aspect, about 0.02 to about 0.075 μg per minute per gram of cells, and in another aspect, about 0.02 to about 0.055 μg per minute per gram of cells; as one example, a specific ethanol productivity of 3 g/L/day/gram of cells would require a Zn feed rate of about 0.04 μg per minute per gram of cells;

Co: in one aspect, about 0.002 to about 0.05 μg per minute per gram of cells, in another aspect, about 0.002 to about 0.04 μg per minute per gram of cells, in another aspect, about 0.002 to about 0.03 μg per minute per gram of cells, in another aspect, about 0.002 to about 0.02 μg per minute per gram of cells, in another aspect, about 0.005 to about 0.035 μg per minute per gram of cells, in another aspect, about 0.005 to about 0.025 μg per minute per gram of cells, in another aspect, about 0.01 to about 0.035 μg per minute per gram of cells, and in another aspect, about 0.01 to about 0.025 μg per minute per gram of cells; as one example, a specific ethanol productivity of 3 g/L/day/gram of cells would require a Co feed rate of about 0.018 μg per minute per gram of cells;

Ni: in one aspect, about 0.003 to about 0.055 μg per minute per gram of cells, in another aspect, about 0.003 to about 0.045 μg per minute per gram of cells, in another aspect, about 0.003 to about 0.035 μg per minute per gram of cells, in another aspect, about 0.003 to about 0.02 μg per minute per gram of cells, in another aspect, about 0.005 to about 0.04 μg per minute per gram of cells, in another aspect, about 0.005 to about 0.03 μg per minute per gram of cells, in another aspect, about 0.01 to about 0.04 μg per minute per gram of cells, and in another aspect, about 0.01 to about 0.03 μg per minute per gram of cells; as one example, a specific ethanol productivity of 3 g/L/day/gram of cells would require a Ni feed rate of about 0.02 μg per minute per gram of cells;

W: in one aspect, about 0.035 to about 0.80 μg per minute per gram of cells, in another aspect, about 0.035 to about 0.65 μg per minute per gram of cells, in another aspect, about 0.035 to about 0.47 μg per minute per gram of cells, in another aspect, about 0.035 to about 0.30 μg per minute per gram of cells, in another aspect, about 0.075 to about 0.55 μg per minute per gram of cells, in another aspect, about 0.075 to about 0.40 μg per minute per gram of cells, in another aspect, about 0.155 to about 0.55 μg per minute per gram of cells, and in another aspect, about 0.155 to about 0.40 μg per minute per gram of cells; as one example, a specific ethanol productivity of 3 g/L/day/gram of cells would require a W feed rate of about 0.29 μg per minute per gram of cells;

Se: in one aspect, about 0.001 to about 0.03 μg per minute per gram of cells, in another aspect, about 0.035 to about 0.65 μg per minute per gram of cells, in another aspect, about 0.035 to about 0.47 μg per minute per gram of cells, in another aspect, about 0.035 to about 0.30 μg per minute per gram of cells, in another aspect, about 0.075 to about 0.55 μg per minute per gram of cells, in another aspect, about 0.075 to about 0.40 μg per minute per gram of cells, in another aspect, about 0.155 to about 0.55 μg per minute per gram of cells, and in another aspect, about 0.155 to about 0.40 μg per minute per gram of cells; as one example, a specific ethanol productivity of 3 g/L/day/gram of cells would require a Se feed rate of about 0.01 μg per minute per gram of cells.

In another aspect, the fermentation medium is provided with about 0.006 μg or more per minute of N per gram of cells, about 0.025 μg or more per minute of P per gram of cells, and about 0.001 μg or more per minute of K per gram of cells. In this aspect, the fermentation medium may include the following amounts of one or more of the following:

N: in one aspect, about 0.006 to about 0.12 μg per minute per gram of cells, in another aspect, about 0.006 to about 0.095 μg per minute per gram of cells, in another aspect, about 0.006 to about 0.07 μg per minute per gram of cells, in another aspect, about 0.006 to about 0.045 μg per minute per gram of cells, in another aspect, about 0.01 to about 0.085 μg per minute per gram of cells, in another aspect, about 0.01 to about 0.06 μg per minute per gram of cells, in another aspect, about 0.02 to about 0.085 μg per minute per gram of cells, and in another aspect, about 0.02 to about 0.06 μg per minute per gram of cells; as one example, a specific ethanol productivity of 3 g/L/day/gram of cells would require a N feed rate of about 0.044 μg per minute per gram of cells;

P: in one aspect, about 0.025 to about 0.55 μg per minute per gram of cells, in another aspect, about 0.025 to about 0.45 μg per minute per gram of cells, in another aspect, about 0.025 to about 0.35 μg per minute per gram of cells, in another aspect, about 0.025 to about 0.20 μg per minute per gram of cells, in another aspect, about 0.05 to about 0.38 μg per minute per gram of cells, in another aspect, about 0.05 to about 0.27 μg per minute per gram of cells, in another aspect, about 0.1 to about 0.38 μg per minute per gram of cells, and in another aspect, about 0.1 to about 0.3 μg per minute per gram of cells; as one example, a specific ethanol productivity of 3 g/L/day/gram of cells would require a P feed rate of about 0.2 μg per minute per gram of cells;

K: in one aspect, about 0.001 to about 25 μg per minute per gram of cells, in another aspect, about 0.001 to about 0.03 μg per minute per gram of cells, in another aspect, about 0.001 to about 0.025 μg per minute per gram of cells, in another aspect, about 0.001 to about 0.02 μg per minute per gram of cells, in another aspect, about 0.001 to about 0.01 μg per minute per gram of cells, in another aspect, about 0.003 to about 0.02 μg per minute per gram of cells, in another aspect, about 0.003 to about 0.015 μg per minute per gram of cells, in another aspect, about 0.005 to about 0.02 μg per minute per gram of cells, and in another aspect, about 0.005 to about 0.015 μg per minute per gram of cells; as one example, a specific ethanol productivity of 3 g/L/day/gram of cells would require a K feed rate of about 0.01 μg per minute per gram of cells;

In another aspect, the fermentation medium includes less than about 0.02 weight % $NaHCO_3$, in another aspect, less than about 0.01 weight % $NaHCO_3$, and in another aspect, less than about 0.005 weight percent $NaHCO_3$. $NH_4OH$ may be utilized for pH adjustment in place of $NaHCO_3$. Low phosphate levels alone or in combination with reduced usage of $NaHCO_3$ results in lower medium conductivity. Lowered medium conductivity requires less dilution and reduced water requirements as described. In a related aspect, the fermentation medium has a pH of about 4.2 to about 4.8.

CO feed rates may be expressed in standard cubic feet per minute (SCFM) or in standard cubic feet per hour per liter. In this aspect, the standard cubic feet per hour per liter may be in a range of about 0.9 to about 2.0, and in another aspect, about 1.25 to about 1.75 SCFM. In another aspect, the average CO feed rate is a CO feed rate effective for maintaining a ratio of CO feed rate to fermentor volume of about 0.016:1 to about 0.04:1, in another aspect, about 0.02:1 to about 0.04:1, in another aspect, about 0.02:1 to about 0.035:1, in another aspect, about 0.025:1 to about 0.035:1, and in another aspect, about 0.025:1 to about 0.03:1.

In another aspect, the process includes monitoring the $H_2$ conversion and maintaining an $H_2$ conversion of about 25% or more, in another aspect, about 25% to about 95%, in another aspect, about 30% to about 90%, in another aspect, about 35% to about 85%, in another aspect, about 40% to about 80%, in another aspect, about 40% to about 70%, in another aspect, about 40% to about 60%, and in another aspect, about 40% to about 50%. The process may further include monitoring CO uptake and maintaining a CO uptake of about 0.001 to about 10 mmole/minute/gram of dry cells, in another aspect, about 0.001 to about 5 mmole/minute/gram of dry cells, in another aspect, about 0.001 to about 4 mmole/minute/gram of dry cells, in another aspect, about 0.001 to about 3 mmole/minute/gram of dry cells, in another aspect, about 0.001 to about 2 mmole/minute/gram of dry cells, in another aspect, about 0.001 to about 1 mmole/minute/gram of dry cells, in another aspect, about 0.05 to about 9 mmole/minute/gram of dry cells, in another aspect, about 0.05 to about 5 mmole/minute/gram of dry cells, in another aspect, about 0.05 to about 4 mmole/minute/gram of dry cells, in another aspect, about 0.05 to about 3 mmole/minute/gram of dry cells, in another aspect, about 0.05 to about 2 mmole/minute/gram of dry cells, in another aspect, about 0.05 to about 1 mmole/minute/gram of dry cells, in another aspect, about 1 to about 8 mmole/minute/gram of dry cells, in another aspect, about 1 to about 5 mmole/minute/gram of dry cells, in another aspect, about 1 to about 4 mmole/minute/gram of dry cells, in another aspect, about 1 to about 3 mmole/minute/gram of dry cells, and in another aspect, about 1 to about 2 mmole/minute/gram of dry cells.

EXAMPLES

Example 1: Compatibility Testing

A previously utilized trace metals solution included the following components (all expressed in grams/liter).

|  | Stock | Compatibility Test |
|---|---|---|
| 1) $ZnSO_4 \cdot 7H_2O$ | 0.5222 | 2.35 |
| 2) $COCl_2 \cdot 6H_2O$ | 1.6 | 7.196 |
| 3) $NiCl_2 \cdot 6H_2O$ | 0.4944 | 2.222 |
| 4) $Na_2SeO_3$ | 0.16 | 0.72 |
| 5) $Na_2WO_4 \cdot 2H_2O$ | 3.2 | 14.404 |
| 6) $H_3PO_4$ (85%) | 10% | N/A |

An acidic matrix is necessary to keep all the above 5 trace metals in one solution. However, these metals by themselves are highly soluble in water. Therefore a compatible test was done as described below. Individual solutions of each trace metal were made. The concentration of each solution was equal to the concentration of each trace metal in the stock solution. Each solution was mixed with each of the other and incubated overnight at room temperature. The following morning solutions were visually inspected for turbidity and the optical density of the (vortexed) solutions were measured on a spectrophotometer. Results are shown below.

|  | 1 | 2 | 3 | 4 | 5 |
|---|---|---|---|---|---|
|  |  | C | C | C | T |
| 1 |  | 0.007 | 0.016 | 0.001 | 0.487 |
|  |  |  | C | ST | T |
| 2 |  |  | 0.004 | 0.025 | 0.736 |
|  |  |  |  | ST | C |
| 3 |  |  |  | 0.051 | 0.001 |
|  |  |  |  |  | C |
| 4 |  |  |  |  | 0.002 |

C—Clear
ST—slightly turbid
T—Turbid
1, 2, 3—C 0.002

The above data indicate that an acid matrix is needed to keep Se and W protonated so that they will not form precipitates with Zn, Co and Ni. Based above findings, instead of one trace metal stock solution two trace metal stock solutions were made. A first stock solution included Zn, Co, and Ni and a second stock solution included W and Se. This preparation method reduces the use of $H_3PO_4$. In order to compensate for a complete elimination of phosphoric acid in the lab stock solution, an amount of phosphoric acid addition to the first stock solution was increased from 0.075 ml/L to 0.2 ml/L. Therefore the total net reduction of $H_3PO_4$ in the medium was 76%.

Example 2: Use of Reduced Phosphate Medium

The above mentioned (containing 76% less phosphoric acid) medium was tested on a steady state culture in 4 stages as follows.

1. Modified medium replaced existing media on steady culture (T=0 hrs).
2. $NH_4Cl$ in the growth medium was replaced with $NH_4OH$. As a precautionary measure $H_2SO_4$ was added to the growth medium to maintain pH of the reactor at 4.5 (T=108.74 hrs).
3. $H_2SO_4$ was removed from the medium and $NaHCO_3$ was replaced with $NH_4OH$ as the base to control pH of the reactor (T=158.42 hrs).
4. Components in the first stock solution were directly added to the fermentation medium (T=489.07 hrs).

FIG. 1 shows performance of a steady state *Clostridium ljungdahlii* culture on a low phosphate medium and the use of $NH_4OH$ as base to control pH and act as a nitrogen source. Events during fermentation were as follows.

| Event No. | Time (hrs) | Action |
|---|---|---|
| 1 | 0 | Medium changed to low phosphate medium (2.92 mM $H_3PO_4$) |
| 2 | 59.82 | Medium changed to low phosphate medium (4.38 mM $H_3PO_4$) |
| 3 | 108.74 | Medium changed to low phosphate medium (2.93 mM $H_3PO_4$) containing $H_2SO_4$, started 182 mM $NH_4OH$ pump at 0.4 ml/min. |
| 4 | 135.32 | Base solution changed from 7.7% $NaHCO_3$ to 182 mM $NH_4OH \cdot NH_4OH$ pump solution changed from 182 mM to 92 mM |
| 5 | 135.41 | Increased $NH_4OH$ pump flow rate from 0.3 ml/min to 0.5 ml/min |
| 6 | 158.42 | Medium changed to low phosphate medium (2.92 mM $H_3PO_4$), no $NH_4Cl$, no $H_2SO_4$ |
| 7 | 158.47 | Decreased $NH_4$ pump to 0.5 from 0.6 ml/min |
| 8 | 181.49 | Decreased $NH_4$ pump to 0.4 from 0.5 ml/min |
| 9 | 224.74 | Decreased $NH_4$ pump to 0.2 from 0.4 ml/min |
| 10 | 250.09 | Base solution changed to 364 mM from 182 mM |

-continued

| Event No. | Time (hrs) | Action |
|---|---|---|
| 11 | 255.86 | NH$_4$ pump stopped |
| 12 | 261.61 | 5 mL 0.5M NH$_4$ solution added |
| 13 | 264.74 | NH$_4$ pump restarted at 0.2 ml/min |
| 14 | 270.57 | NH$_4$ pump stopped |
| 15 | 279.32 | Increased vitamin concentration to 1 ml/L from 0.5 ml/L |
| 16 | 280.66 | Changed base solution to 0.5M from 364 mM |
| 17 | 392.22 | Decreased permeate flow to reduce cell density. Target 3 g/L |
| 18 | 441.82 | Increased vitamin concentration to 1.6 ml/L from 1.0 ml/L |
| 19 | 489.07 | Medium changed to low phosphate medium with first stock solution components added as dry powder and second stock solution added in aqueous form |

At 108.74 hrs, media containing 0.35 ml/L H$_2$SO$_4$ (75%) was added to the reactor. NH$_4$Cl was removed from the media and the NH$_4$OH pump was started. This was done in order to insure that the additional base being pumped into the reactor would not overshoot the pH set-point. The amount added was calculated based on the amount of protons eliminated as H$_3$PO$_4$, taking into account that H$_3$PO$_4$ was mono-protic at this pH and H$_2$SO$_4$ was di-protic. It was later confirmed that the culture was still using base and the H$_2$SO$_4$ was eliminated.

Starting at 135.32 hrs, the base solution of NaHCO$_3$ was replaced with NH$_4$OH. The concentration of the base was adjusted along with the flow rate of the NH$_4$OH pump until a final solution of 0.5M was settled upon. Using this concentration there was no need to add supplemental NH$_4$OH to provide nitrogen to the culture.

Between 279.32 hrs and 441.82 hrs the concentration of vitamins in the medium was increased to 1.6 ml/L.

At 392.22 hrs the cell density was decreased to 3 g/L.

The final media composition change was made at 489.07 hrs which was done by adding the first stock solution components directly to the medium in their solid form (as done with all other components). The second stock solution components were added as an aqueous solution.

While the invention herein disclosed has been described by means of specific embodiments, examples and applications thereof, numerous modifications and variations could be made thereto by those skilled in the art without departing from the scope of the invention set forth in the claims.

What is claimed is:

1. A fermentation process comprising:
blending a liquid medium that includes at least one transition metal element with a second liquid medium that includes at least one other transition metal element and optionally one non-metal element to provide a fermentation medium where precipitation of the at least one or more transition metal element, the at least one other transition metal element and the one or more non-metal elements if present is prevented, and where the fermentation medium has a conductivity of 30 mS/cm or less;
contacting a CO-containing substrate with the fermentation medium; and
fermenting the CO-containing substrate with acetogenic bacteria to provide an acidic pH,
wherein the fermentation medium includes 3 mM or less phosphate, and
wherein the fermentation process utilizes 2 US gallons of water or less provided to the fermentation medium per US gallon of ethanol produced.

2. The fermentation process of claim 1, wherein the transition metal element is selected from the group consisting of one or more of W, Zn, Co and Ni.

3. The fermentation process of claim 1 wherein the non-metal element is Se.

4. The fermentation process of claim 1 wherein fermentation is effective for providing a pH of about 4.2 to about 4.8.

5. The fermentation process of claim 1 wherein the blend of at least one transition metal element and at least one non-metal element has an optical density of about 0.7 or less at 580 nm.

6. The process of claim 1 wherein the CO-containing substrate provided to the fermentor has a CO/CO$_2$ molar ratio of about 0.75 or more.

7. The process of claim 1 wherein the process is effective for providing an STY of 10 g total alcohol/(L·day) or more.

8. The process of claim 1 wherein the process includes fermenting the CO-containing substrate with an acetogenic bacteria selected from the group consisting of *Acetogenium kivui, Acetoanaerobium noterae, Acetobacterium woodii, Alkalibaculum bacchi* CP11 (ATCC BAA-1772), *Blautia producta, Butyribacterium methylotrophicum, Caldanaerobacter subterraneous, Caldanaerobacter subterraneous pacificus, Carboxydothermus hydrogenoformans, Clostridium aceticum, Clostridium acetobutylicum, Clostridium acetobutylicum* P262 *Clostridium autoethanogenum* (DSM 19630 of DSMZ Germany), *Clostridium autoethanogenum* (DSM 10061 of DSMZ Germany), *Clostridium autoethanogenum* (DSM 23693 of DSMZ Germany), *Clostridium autoethanogenum* (DSM 24138 of DSMZ Germany), *Clostridium carboxidivorans* P7 (ATCC PTA-7827), *Clostridium coskatii* (ATCC PTA-10522), *Clostridium drakei, Clostridium ljungdahlii* PETC (ATCC 49587), *Clostridium ljungdahlii* ERI2 (ATCC 55380), *Clostridium ljungdahlii* C-01 (ATCC 55988), *Clostridium ljungdahlii* O-52 (ATCC 55889), *Clostridium magnum, Clostridium pasteurianum* (DSM 525 of DSMZ Germany), *Clostridium ragsdali* P11 (ATCC BAA-622), *Clostridium scatologenes, Clostridium thermoaceticum, Clostridium ultunense, Desulfotomaculum kuznetsovii, Eubacterium limosum, Geobacter sulfurreducens, Methanosarcina acetivorans, Methanosarcina barkeri, Morrella thermoacetica, Morrella thermoautotrophica, Oxobacter pfennigii, Peptostreptococcus productus, Ruminococcus productus, Thermoanaerobacter kivui,* and mixtures thereof.

9. The fermentation process of claim 1 wherein the fermentation medium is provided with at least one or more of
about 0.04 µg or more per minute of Zn per gram of cells,
about 0.018 µg or more per minute of Co per gram, of cells,
about 0.02 µg, or more per minute of Ni per gram of cells,
about 0.29 µg or more per minute of W per gram of cells, and
about 0.01 µg or more per minute of Se per gram of cells.

10. The fermentation process of claim 1 wherein the fermentation medium includes less than about 0.02 weight % NaHCO$_3$.

11. The fermentation process of claim 1 wherein the fermentation medium is provided with at least one or more of
about 0.044 µg or more of nitrogen per gram of cells,
about 0.2 µg or more of phosphorous per gram of cells, or
about 0.01 µg or more of potassium per gram of cells.

12. The process of claim 1 wherein total alcohol includes about 75 weight percent or more ethanol.

13. The process of claim 1 wherein the total alcohol includes about 25 weight percent or less butanol.

* * * * *